(12) United States Patent
Nakatsuji et al.

(10) Patent No.: US 12,248,742 B2
(45) Date of Patent: Mar. 11, 2025

(54) SUPPORT METHOD FOR METAL MATERIAL, PREDICTION MODEL GENERATION METHOD, METAL MATERIAL PRODUCTION METHOD, AND DESIGN SUPPORT APPARATUS

(71) Applicant: JFE STEEL CORPORATION, Tokyo (JP)

(72) Inventors: Kazuhiro Nakatsuji, Tokyo (JP); Osamu Yamaguchi, Tokyo (JP); Hiroyuki Takagi, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 903 days.

(21) Appl. No.: 17/424,164

(22) PCT Filed: Dec. 2, 2019

(86) PCT No.: PCT/JP2019/047091
§ 371 (c)(1),
(2) Date: Jul. 20, 2021

(87) PCT Pub. No.: WO2020/152993
PCT Pub. Date: Jul. 30, 2020

(65) Prior Publication Data
US 2022/0100932 A1 Mar. 31, 2022

(30) Foreign Application Priority Data

Jan. 21, 2019 (WO) .................. PCT/JP2019/001675

(51) Int. Cl.
*G06F 30/27* (2020.01)
*B22D 11/16* (2006.01)
(Continued)

(52) U.S. Cl.
CPC .............. *G06F 30/27* (2020.01); *B22D 11/16* (2013.01); *C22F 1/00* (2013.01); *G06F 18/214* (2023.01); *G06V 10/443* (2022.01)

(58) Field of Classification Search
CPC ..... G06F 30/27; G06F 18/214; G06V 10/443; C22F 1/00; B22D 11/16
(Continued)

(56) References Cited

U.S. PATENT DOCUMENTS 6,411,945 B1 * 6/2002 Nakajima ................. B60C 1/00
703/2
8,374,981 B2 * 2/2013 Shigemori ............. G06Q 10/04
706/45

(Continued)

FOREIGN PATENT DOCUMENTS

JP 2008097607 A 4/2008
JP 2010106314 A 5/2010
(Continued)

OTHER PUBLICATIONS

Dey et al. (An Informatics Based Approach to Reduce the Grain Size of Cast Hadfield Steel, J. Inst. Eng. India Ser. D (Jan.-Jun. 2016) 97(1):1-9). (Year: 2016).*

(Continued)

Primary Examiner — Iftekhar A Khan
(74) Attorney, Agent, or Firm — KENJA IP LAW PC

(57) ABSTRACT

A design support method capable of accurately obtaining predicted values, while also considering production conditions of a metal material, and of reducing the time required for design is provided. The design support method uses a calculator to support design of metal material with desired characteristics and includes searching for design conditions yielding the desired characteristics using a prediction model for predicting a characteristic value of the metal material (Continued)

from the design conditions, the prediction model being constructed based on past performance data associating the design conditions, including chemical composition and production conditions of the metal material, with the characteristic value. The design support method also includes presenting at least the chemical composition and production conditions among the design conditions that are searched for and correspond to the desired characteristics. The design conditions are searched for so that deviation among predicted values based on different training data sets is reduced.

10 Claims, 10 Drawing Sheets

(51) Int. Cl.
　　　C22F 1/00　　　　(2006.01)
　　　G06F 18/214　　(2023.01)
　　　G06V 10/44　　　(2022.01)
(58) Field of Classification Search
　　　USPC .............................................................. 703/1
　　　See application file for complete search history.

(56) References Cited

U.S. PATENT DOCUMENTS

| | | | |
|---|---|---|---|
| 8,756,092 | B1 | 6/2014 | Marsten |
| 10,345,252 | B2* | 7/2019 | Vecchio ................ G01N 25/18 |
| 10,379,448 | B2* | 8/2019 | Mathijssen ......... G03F 7/70525 |
| 10,872,682 | B2* | 12/2020 | Reed ........................ G16C 20/50 |
| 11,216,938 | B2* | 1/2022 | Pu ............................. G06T 5/70 |
| 11,347,910 | B1* | 5/2022 | Martiny .................. G06F 30/27 |
| 11,391,677 | B2* | 7/2022 | Witte ..................... G01J 1/4257 |
| 12,066,417 | B2* | 8/2024 | Eto ...................... G05B 13/0265 |
| 2008/0089591 | A1 | 4/2008 | Zhou et al. |
| 2009/0291013 | A1* | 11/2009 | Fedchun ................. C22C 38/42 148/621 |
| 2012/0283861 | A1* | 11/2012 | Zwickl ................. G05B 19/404 700/97 |
| 2014/0236548 | A1* | 8/2014 | Conduit ................ G16C 20/30 703/2 |
| 2015/0106035 | A1* | 4/2015 | Vecchio ................ G16C 20/30 702/30 |
| 2015/0170022 | A1* | 6/2015 | Malik ..................... G06F 30/23 706/21 |
| 2016/0034614 | A1* | 2/2016 | Wang ...................... G06F 30/27 703/2 |
| 2016/0282282 | A1* | 9/2016 | Quintanilha ....... G01N 21/8806 |
| 2017/0002440 | A1* | 1/2017 | Sprock ..................... B21B 37/74 |
| 2017/0045823 | A1* | 2/2017 | Quintanilha .............. G03F 1/24 |
| 2017/0297072 | A1* | 10/2017 | Kuyama ................ C21D 11/00 |
| 2018/0018408 | A1* | 1/2018 | Matsumura ............ G06F 30/00 |
| 2018/0113967 | A1* | 4/2018 | Agrawal ............ G01N 33/2022 |
| 2018/0348145 | A1* | 12/2018 | Witte ....................... G03F 7/706 |
| 2019/0228327 | A1* | 7/2019 | Horesh ............. G05B 13/0265 |
| 2019/0271966 | A1* | 9/2019 | Coffman .................. G06N 5/04 |
| 2020/0020415 | A1 | 1/2020 | Sarmiento et al. |
| 2020/0024712 | A1* | 1/2020 | Iwamura ................ B22D 2/006 |
| 2020/0089826 | A1* | 3/2020 | Liu ......................... G06F 30/27 |
| 2020/0257933 | A1* | 8/2020 | Steingrimsson .......... B22B 5/04 |
| 2021/0334440 | A1* | 10/2021 | Yamashina .............. G06N 3/08 |
| 2021/0397769 | A1* | 12/2021 | Okuno ....................... C22C 1/00 |
| 2021/0406433 | A1* | 12/2021 | Okuno ....................... G16C 60/00 |
| 2022/0072593 | A1* | 3/2022 | Fujita .................. G05B 19/4097 |
| 2022/0076161 | A1* | 3/2022 | Takada .................... G06N 20/00 |
| 2022/0207218 | A1* | 6/2022 | Lu ............................. G06N 3/08 |
| 2022/0276619 | A1* | 9/2022 | Moriguchi ......... G05B 13/0265 |
| 2022/0292229 | A1* | 9/2022 | Aonuma ................. G06F 30/10 |
| 2024/0136026 | A1* | 4/2024 | Takemoto .............. G06N 20/10 |
| 2024/0144056 | A1* | 5/2024 | Huang ................... G16H 50/30 |

FOREIGN PATENT DOCUMENTS

| | | | |
|---|---|---|---|
| JP | 2010172962 A | 8/2010 | |
| JP | 2011103036 A | 5/2011 | |
| JP | 2012146054 A | 8/2012 | |
| KR | 101011546 B1 | 1/2011 | |
| RU | 2016116261 A | 11/2017 | |
| WO | 2018062398 A1 | 4/2018 | |
| WO | WO-2020152993 A1 * | 7/2020 | ............. B22D 11/16 |

OTHER PUBLICATIONS

Reddy et al. (Design of medium carbon steels by computational intelligence Techniques, Computational Materials Science 101 (2015) 120-126). (Year: 2015).*

Mar. 10, 2022, the Extended European Search Report issued by the European Patent Office in the corresponding European Patent Application No. 19911629.4.

N.S. Reddy et al., Design of medium carbon steels by computational intelligence techniques, Computational Materials Science, 2015, pp. 120-126, vol. 101.

Santanu Pattanayak et al., Computational intelligence based designing of microalloyed pipeline steel, Computational Materials Science, 2015, pp. 60-68, vol. 104.

Swati Dey et al., An Informatics Based Approach to Reduce the Grain Size of Cast Hadfield Steel, Journal of The Institution of Engineers (India): Series D, Jul. 19, 2015, pp. 1-9, vol. 97.

Apr. 22, 2022, Office Action issued by the Federal Service for Intellectual Property, Patents and Trademarks of the Russian Federation in the corresponding Russian Patent Application No. 2021124646 with English language search report.

Sep. 20, 2023, Office Action issued by the Korean Intellectual Property Office in the corresponding Korean Patent Application No. 10-2021-7025687 with English language concise statement of relevance.

Hiroshi Hasegawa, From Demands and Wishes to the Optimal Design Using the Systems Approach, Proceedings of the 28th Japan simulation conference, Jun. 11, 2009, pp. 113-116, with a partial English translation.

Jun. 15, 2021, Notification of Reasons for Refusal issued by the Japan Patent Office in the corresponding Japanese Patent Application No. 2020-516503 with English language Concise Statement of Relevance.

Mar. 3, 2020, International Search Report issued in the International Patent Application No. PCT/JP2019/047091.

Seiji Takeda et al., Material discovery by AI, The 32nd Annual Conference of the Japanese Society for Artificial Intelligence, 2018, with a partial English translation.

Yoshitaka Adachi et al., Material Information General System for Machine Learning Support, Systems, Control and Information, 2017, pp. 188-193, vol. 61, Issue 5, with a partial English translation.

* cited by examiner (0.11, 0.47, 0.94, 0.83)

(0.10, 0.31, 0.54, 0.89)

(0.56, 0.91, 0.35, 0.92)

(0.41, 0.91, 0.38, 0.20)

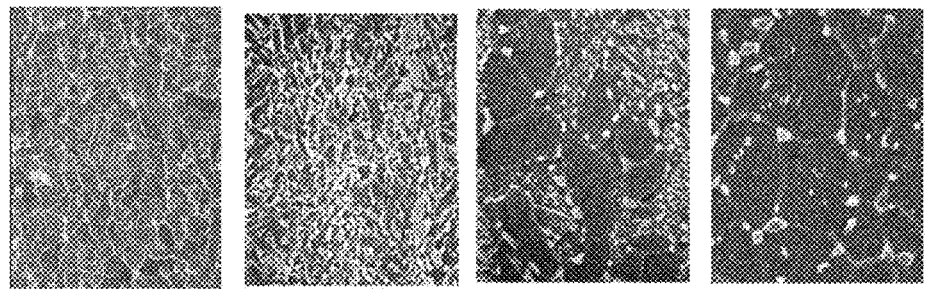

SUPPORT METHOD FOR METAL MATERIAL, PREDICTION MODEL GENERATION METHOD, METAL MATERIAL PRODUCTION METHOD, AND DESIGN SUPPORT APPARATUS

TECHNICAL FIELD

The present disclosure relates to a design support method for a metal material with desired characteristics, a prediction model generation method, a metal material production method, and a design support apparatus.

BACKGROUND

When designing a new material, a user engages in trial and error by repeating the steps of establishing design conditions based on experience and revising the design based on the results of experimentally producing material. It thus takes time for the user to learn the results of the design. Consequently, the time required to design a material with sufficient characteristics increases. Moreover, the design content depends on the user's experience, and the user's accumulated experience may, in some cases, impede innovation.

Recently, the accuracy of prediction models using machine learning has significantly increased. To reduce the above-described required time, machine learning techniques have been used to support development of new materials. The predicted values of characteristics of a material can be learned with a prediction model before experimental production. A reduction in the time required for development is therefore expected. For example, patent literature (PTL) 1 discloses a method for searching for optimal design conditions by repeating the process of calculating characteristic values with a physical simulation and updating a forward model.

A technique for predicting design conditions to obtain material with desired characteristics by applying a prediction model and performing back analysis has also been proposed. For example, PTL 2 discloses a method for using a neural network to perform back analysis of production conditions for aluminum that has desired characteristic values. The learning results of the neural network in PTL 2 are obtained within a condition range of a training data set, and PTL 2 states that the neural network cannot make predictions outside of the condition range. In other words, PTL 2 proposes performing back analysis while expressly not searching for production conditions that diverge from the training data set. Non-patent literature (NPL) 1 discloses a method to construct a prediction model for predicting characteristic values from the chemical structure of an organic compound and to identify the chemical structure of an organic compound that has desired characteristics by back analysis.

CITATION LIST

Patent Literature

PTL 1: JP 2011-103036 A
PTL 2: WO2018/062398

Non-Patent Literature

NPL 1: "Material discovery by AI", TAKEDA Seiji et al., 32$^{nd}$ Annual Conference of the Japanese Society for Artificial Intelligence, 2018, 3E1-02

SUMMARY

Technical Problem

The method in PTL 1, however, uses an electromagnetic field analysis model to calculate characteristic values. The calculation time therefore increases, and searches cannot be sufficiently performed. The method disclosed in PTL 2 does not search for production conditions that diverge from the training data set. Proposals therefore cannot be made in areas of new production conditions but rather remain in a narrow area based on conventional production conditions. Furthermore, deviation among a plurality of predicted values based on a plurality of training data sets is not evaluated, making it difficult to obtain predicted values accurately while reducing such deviation. Unlike the method to identify the chemical structure of an organic compound in NPL 1, various production conditions including heat treatment temperature and the like affect the characteristic values of a metal material during the design of the metal material. Accordingly, a prediction model that also takes into consideration production conditions of the metal material as design conditions of the design target needs to be constructed.

In light of these problems, the present disclosure aims to provide a design support method, a prediction model generation method, a metal material production method, and a design support apparatus that can obtain accurate prediction values and reduce the time required for design, while also taking production conditions of a metal material into account.

Solution to Problem

A design support method according to an embodiment of the present disclosure for solving the aforementioned problem is a design support method for supporting design, with use of a calculator, of a metal material that has desired characteristics, the design support method including:
  searching for design conditions that yield the desired characteristics using a prediction model for predicting a characteristic value of the metal material from the design conditions, the prediction model being constructed based on past performance data associating the design conditions, which include a chemical composition and production conditions of the metal material, with the characteristic value; and
  presenting at least the chemical composition and the production conditions among the design conditions that are searched for and correspond to the desired characteristics, wherein
  the design conditions are searched for so that deviation among a plurality of predicted values based on a plurality of different training data sets is reduced.

A prediction model generation method according to an embodiment of the present disclosure for solving the aforementioned problem is a prediction model generation method for generating the prediction model used in the aforementioned design support method and includes:
  acquiring the past performance data associating the design conditions with the characteristic value; and
  constructing the prediction model, for predicting the characteristic value from the design conditions, based on the acquired past performance data.

A metal material production method according to an embodiment of the present disclosure for solving the aforementioned problem includes producing the metal material based on the design conditions searched for by the aforementioned design support method.

A design support apparatus according to an embodiment of the present disclosure for solving the aforementioned problem is a design support apparatus for supporting design of a metal material that has desired characteristics, the design support apparatus including:

a search unit configured to search for design conditions that yield the desired characteristics using a prediction model for predicting a characteristic value of the metal material from the design conditions, the prediction model being constructed based on past performance data associating the design conditions, which include a chemical composition and production conditions of the metal material, with the characteristic value; and a presentation interface configured to present at least the chemical composition and the production conditions among the design conditions, searched for by the search unit, that correspond to the desired characteristics, wherein the search unit searches for the design conditions so that deviation among a plurality of predicted values based on a plurality of different training data sets is reduced.

Advantageous Effect

The design support method, the prediction model generation method, the metal material production method, and the design support apparatus according to an embodiment of the present disclosure can reduce the time required for design while also taking production conditions of a metal material into account.

BRIEF DESCRIPTION OF THE DRAWINGS

In the accompanying drawings:

FIG. 9 is a schematic diagram illustrating an example of a method to convert a feature vector into image data.

DETAILED DESCRIPTION

First Embodiment

A first embodiment of the present disclosure is now described. The metal material to be designed in the first embodiment is, for example, steel. The metal material is not limited to steel, however, and may be any metal.

Figure 1:
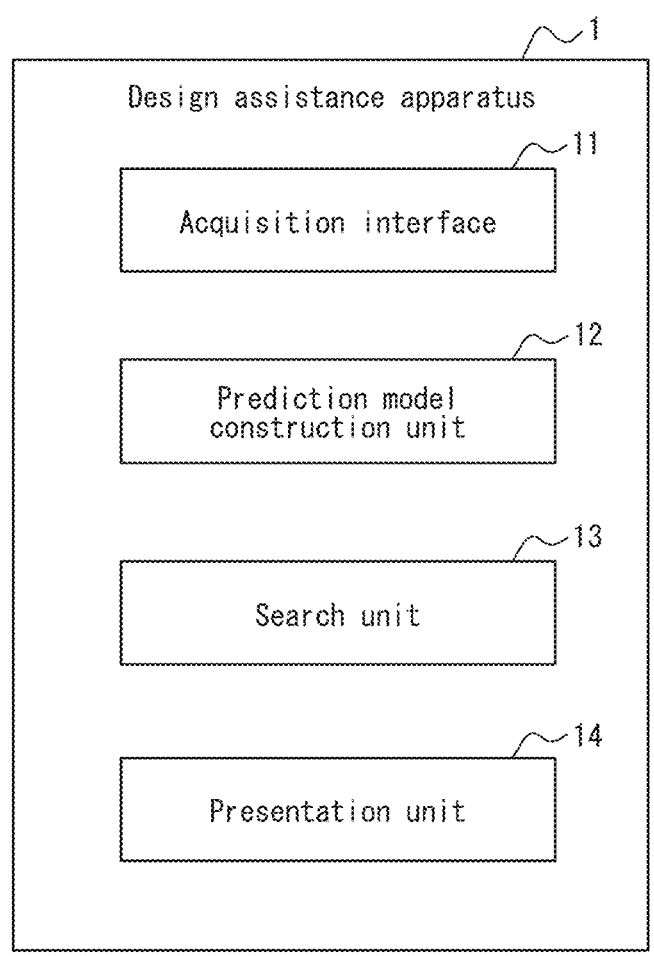
FIG. 1 is a functional block diagram illustrating the configuration of a design support apparatus according to a first embodiment of the present disclosure.

FIG. 1 is a functional block diagram illustrating the configuration of a design support apparatus according to the first embodiment of the present disclosure. As illustrated in FIG. 1, the design support apparatus 1 according to the first embodiment includes an acquisition interface 11, a prediction model construction unit 12, a search unit 13, and a presentation interface 14. The design support apparatus 1 supports the design of a metal material that has desired characteristics.

The acquisition interface 11 acquires past performance data for production of steel material, for example, as necessary for constructing the prediction model described below. The acquisition interface 11 may include a communication interface for acquiring the performance data. In this case, the acquisition interface 11 may, for example, receive the performance data from a plurality of external apparatuses or the like using a predetermined communication protocol. The performance data includes, for example, data associating design conditions, which include the chemical composition and production conditions of steel material, with characteristic values of the steel material. The production conditions include, for example, setting values, performance values, and the like for production conditions.

The data, acquired by the acquisition interface 11, on the chemical composition of the steel material includes, for example, addition ratios of elements to be dissolved as components in steel in a converter or during secondary refining. Examples of such elements include C, Si, Mn, P, S, Al, N, Cr, V, Sb, Mo, Cu, Ni, Ti, Nb, B, Ca, and Sn.

Figure 2:
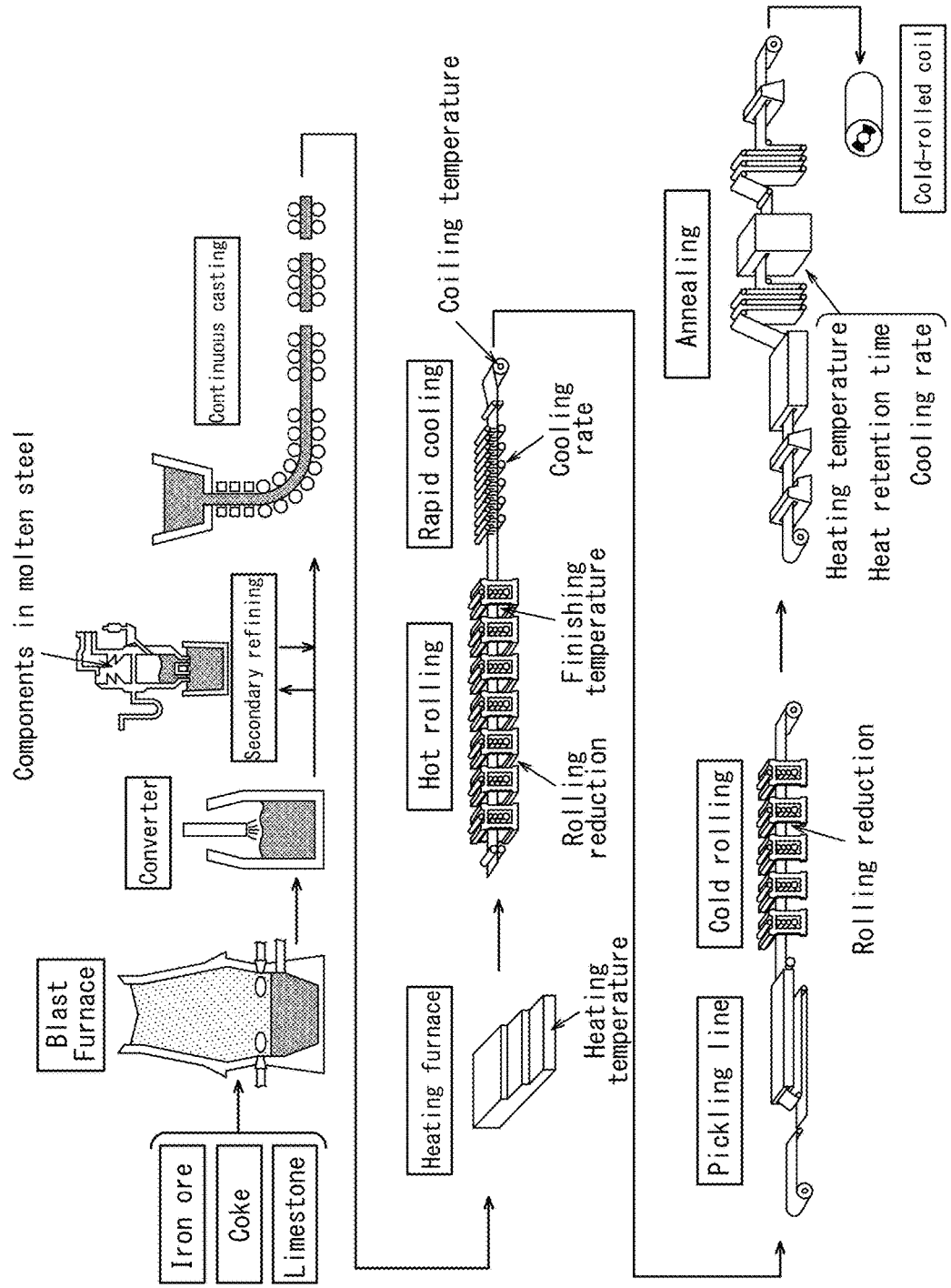
FIG. 2 is a schematic diagram illustrating a process to produce a cold-rolled coil of a steel material according to the first embodiment.

The data on production conditions acquired by the acquisition interface 11 is, for example, based on various conditions in each process during production of steel material. FIG. 2 is a schematic diagram illustrating a process to produce a cold-rolled coil of a steel material according to the first embodiment. During the steel production process of the steel sheet, raw iron ore is first charged into a blast furnace together with limestone and coke to generate molten pig iron. Components, such as carbon, of the pig iron produced in the blast furnace are adjusted in a converter of the steel factory, and final component adjustment is performed by secondary refining. The resulting molten steel is cast by a continuous casting machine or the like to produce a semi-finished product, referred to as a slab, before sheet formation. Subsequently, a plurality of processes are performed in a heating furnace, such as a heating process, a hot rolling process, a cooling process, a pickling process, a cold rolling process, an annealing process and a plating process, to produce a cold-rolled coil as a product. The combination of these processes differs in accordance with the product being produced. Except for conditions related to composition, the characteristics of the steel material are largely determined by the production conditions of post-processes that follow heating of the slab after casting, such as the hot rolling process, the cooling process, the cold rolling process, and the like. The conditions during processes after slab production are taken as an example of production conditions in the first embodiment.

The conditions during the above-described processes, i.e. the production conditions, include the following, for example.

TABLE 1

| Production process | Production condition |
|---|---|
| Heating process | Heating temperature (° C.) |
| Hot rolling process | Rolling reduction |
| | Finishing temperature (° C.) |
| | Cooling rate (° C./s) |
| | Coiling temperature (° C.) |
| Cold rolling process | Rolling reduction |
| Annealing process | Heating temperature (° C.) |
| | Insulation time (s) |
| | Cooling rate (° C./s) |

The data, acquired by the acquisition interface 11, on characteristic values of steel material includes the yield point (N/mm$^2$), tensile strength (N/mm$^2$), elongation (%), r value, n value, hole expansion ratio (%), BH amount (N/mm$^2$), and yield ratio, for example. These characteristic values can be obtained by performing sampling tests to evaluate the characteristics of steel material based on a portion of a produced steel material product, for example.

The acquisition interface 11 manages the acquired performance values of each characteristic value as performance data and manages pieces of performance data in association with each other. In greater detail, the acquisition interface 11 can, in units of produced steel material products, integrally associate performance data on the chemical composition of the steel material, performance data on production conditions, and performance data on characteristic values of the steel material to collect and handle these pieces of data.

During the below-described search for optimal design conditions, the acquisition interface 11 may, for example, acquire constraint conditions including ranges for the chemical composition of the steel material and ranges for production conditions as input information. The constraint conditions may further include ranges of characteristic values of the steel material. The constraint conditions may further include conditions guaranteeing no contradictions among changes, occurring between different processes during production, in physical quantities of a steel sheet. For example, the temperature of the steel sheet decreases across processes, except for the case of a heating process. The constraint conditions may, for example, include a condition constraining the production conditions so as not to contradict this temperature decreasing phenomenon. The acquisition interface 11 may, for example, include an input interface for the user of the steel material to input predetermined constraint conditions as input information.

Figure 3:
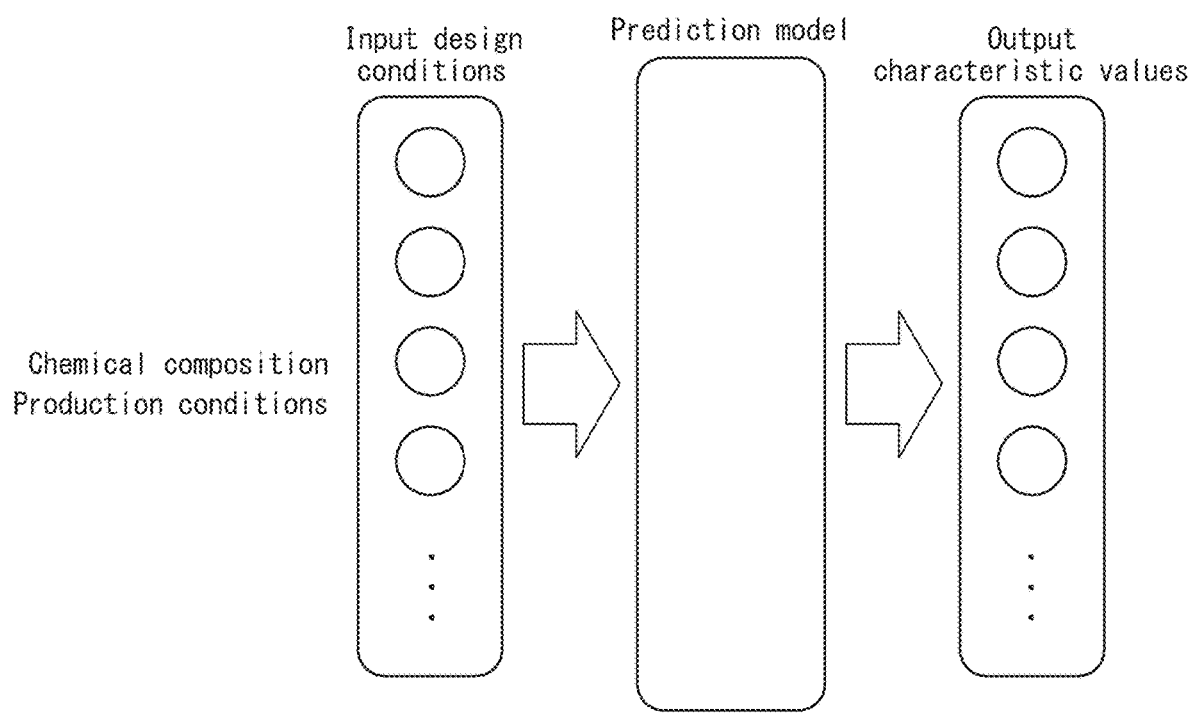
FIG. 3 is a diagram schematically illustrating a prediction model according to the first embodiment.

FIG. 3 is a diagram schematically illustrating a prediction model according to the first embodiment. The prediction model construction unit 12 constructs a prediction model, such as the one illustrated in FIG. 3, that predicts characteristic values of steel material from design conditions based on past performance data acquired by the acquisition interface 11. In greater detail, the prediction model construction unit 12 constructs a prediction model for characteristic values of steel material, using the chemical composition and production conditions of steel material as explanatory variables, based on acquired past performance data. The prediction model includes a model using machine learning technology such as a neural network, a local regression model, a kernel regression model, a random forest, and the like. In the case of a plurality of characteristic values, the prediction model construction unit 12 may select a prediction model capable of handling a plurality of objective variables, such as a neural network, or may construct a prediction model for each characteristic value. The prediction model constructed by the prediction model construction unit 12 is used in the below-described search for optimal design conditions.

Using the prediction model constructed by the prediction model construction unit 12, such as the prediction model illustrated in FIG. 3, that predicts a characteristic value of the steel material from the design conditions, the search unit 13 searches for optimal design conditions that yield desired characteristics. The desired characteristics may be characteristics to maximize a characteristic value for which the maximum value is desired or characteristics to minimize a characteristic value for which the minimum value is desired. Additionally, the desired characteristics may be any other characteristics freely determined by the user in correspondence with the user's product requirements, for example.

The presentation interface 14 presents design conditions, searched for by the search unit 13, corresponding to the desired characteristics to the user. The user can efficiently design steel material by taking the chemical composition and production conditions of the steel material presented by the presentation interface 14 as target values or reference values at the time of producing steel material. When additional conditions other than the chemical composition and production conditions are included in the design conditions, the presentation interface 14 presents at least the chemical composition and production conditions and presents a portion or all of the additional conditions as appropriate.

Figure 4:
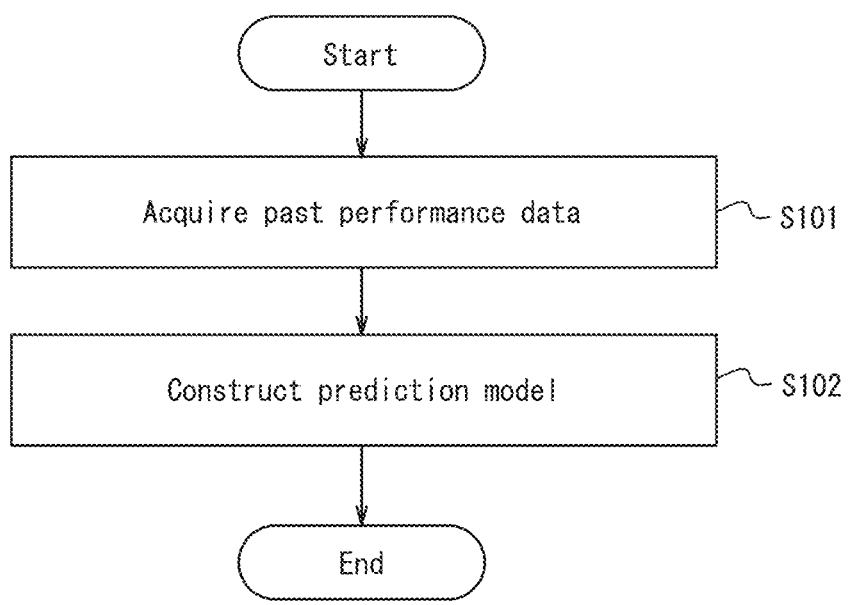
FIG. 4 is a flowchart illustrating a first example of operations by the design support apparatus of FIG. 1.

FIG. 4 is a flowchart illustrating a first example of operations by the design support apparatus 1 of FIG. 1. FIG. 4 illustrates the flow by which the design support apparatus 1 generates a prediction model such as the one illustrated in FIG. 3 based on past performance data.

In step S101, the design support apparatus 1 uses the acquisition interface 11 to acquire past performance data associating design conditions, which include the chemical composition included in steel material and production conditions, with the characteristic values of the steel material.

In step S102, the design support apparatus 1 uses the prediction model construction unit 12 to construct a prediction model that predicts characteristic values of steel material from design conditions based on the past performance data acquired in step S101.

Figure 5:
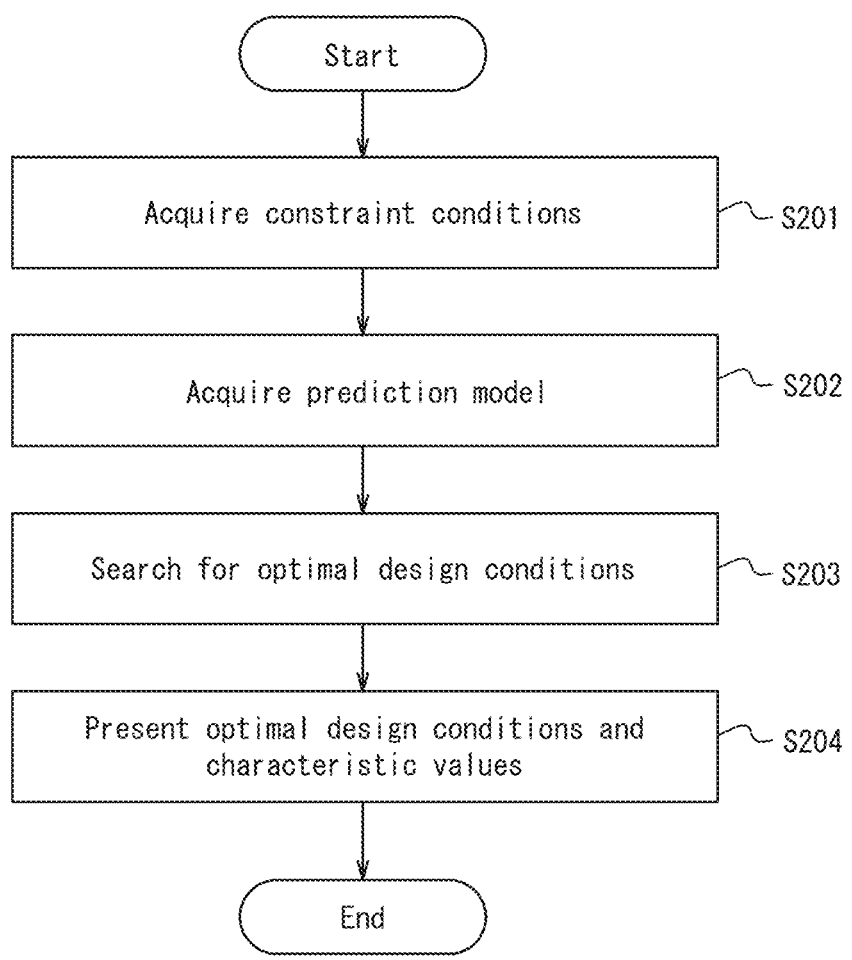
FIG. 5 is a flowchart illustrating a second example of operations by the design support apparatus of FIG. 1.

FIG. 5 is a flowchart illustrating a second example of operations by the design support apparatus 1 of FIG. 1. FIG. 5 illustrates the flow by which the design support apparatus 1 searches for optimal design conditions, using the prediction model generated by the flow in FIG. 4, and presents information to the user.

In step S201, the search unit 13 of the design support apparatus 1 acquires constraint conditions, which include ranges for the chemical composition of the steel material, ranges for production conditions, and ranges for characteristic values of the steel material, for example, as input information from the acquisition interface 11.

In step S202, the search unit 13 of the design support apparatus 1 acquires the above-described prediction model, constructed by the prediction model construction unit 12, from the prediction model construction unit 12.

In step S203, the search unit 13 of the design support apparatus 1 searches for optimal design conditions that yield the desired characteristics for the steel material based on the constraint conditions acquired in step S201 and the prediction model acquired in step S202.

In step S204, the presentation interface 14 of the design support apparatus 1 acquires the optimal design conditions corresponding to the desired characteristics searched for in step S203 and the corresponding characteristic values from the search unit 13 and presents these to the user.

Subsequently, the user produces steel material based on the design conditions searched for in step S203 and presented in step S204.

The content of the processing by the search unit 13 of the design support apparatus 1 in steps S201 through S203 of FIG. 5 is described below in greater detail.

In step S201 of FIG. 5, the search unit 13 acquires constraint conditions, such as those listed in Table 2 below, as input information from the acquisition interface 11. In greater detail, the search unit 13 acquires the upper limit values and lower limit values of the chemical composition of the steel material and the upper limit values and lower limit values of production conditions, i.e. design conditions, as constraint conditions.

TABLE 2

| Production process | Design condition | Lower limit value | Upper limit value |
|---|---|---|---|
| Converter/ secondary refining | C (mass %) | **** | **** |
| | Si (mass %) | **** | **** |
| | Mn (mass %) | **** | **** |
| | P (mass %) | **** | **** |
| | S (mass %) | **** | **** |
| | Cu (mass %) | **** | **** |
| | Ni (mass %) | **** | **** |
| | Cr (mass %) | **** | **** |
| | Sb (mass %) | **** | **** |
| | Sn (mass %) | **** | **** |
| Heating process | Heating temperature (° C.) | **** | **** |
| Hot rolling process | Rolling reduction | **** | **** |
| | Finishing temperature (° C.) | **** | **** |
| | Coiling temperature (° C.) | **** | **** |
| | Cooling rate (° C./s) | **** | **** |
| Cold rolling process | Rolling reduction | **** | **** |
| Annealing process | Heating temperature (° C.) | **** | **** |
| | Insulation time (s) | **** | **** |
| | Cooling rate (° C./s) | **** | **** |

Furthermore, the search unit 13 acquires the upper limit values and lower limit values of the characteristic values of the steel material as constraint conditions.

TABLE 3

| Characteristic | Lower limit value | Upper limit value |
|---|---|---|
| Yield point (N/mm$^2$) | **** | **** |
| Tensile strength (N/mm$^2$) | **** | **** |
| Elongation (%) | **** | **** |
| r value | **** | **** |
| n value | **** | **** |
| Hole expansion ratio (%) | **** | **** |
| BH amount (N/mm$^2$) | **** | **** |
| Yield ratio | **** | **** |

Using the trained prediction model acquired from the prediction model construction unit 12 in step S202 of FIG. 5, the search unit 13 searches for optimal design conditions within the range of the constraint conditions in step S203 of FIG. 5. This problem is an optimization problem and can be described as follows.

$$\max_{x} \sum_{k} \alpha_k f_k(x) \quad \text{(Expression 1)}$$
$$\text{st. } x \in F$$
$$L_k \le f_k \le U_k \quad k = 1..K$$

In Expression 1, x represents the design conditions expressed as a vector, k represents the type of characteristic, $f_k(x)$ represents the predicted value of the characteristic, and $\alpha_k$ represents a weighting factor set in advance. The function $f_k(x)$ for the predicted value of the characteristic in the evaluation function is based on the prediction model constructed by the prediction model construction unit 12. F is a set of design conditions x that satisfy the constraint conditions acquired in step S201. Accordingly, the search unit 13 searches for optimal design conditions within a range that satisfies the constraint conditions. $L_k$, $U_k$ represent the lower limit values and upper limit values of the characteristic values acquired in step S201 of FIG. 5. The search unit 13 solves this optimization problem using a method such as metaheuristics, a genetic algorithm, mathematical programming, or swarm intelligence.

The search unit 13 searches for optimal design conditions by treating the evaluation function in Expression 1 as an optimization problem, but the method of setting the problem is not limited to this example. The search unit 13 may search for optimal design conditions by treating the absolute value of the evaluation function in Expression 1 as an optimization problem, with the sign of the weighting factor $\alpha_k$ being negative, for example. Examples of characteristics for which the maximum value is desired include tensile strength and elongation. Examples of characteristics for which the minimum value is desired include yield ratio.

The search unit 13 calculates the design conditions x obtained by Expression 1 as an optimal solution, but this example is not limiting. The search unit 13 may set a predetermined condition on the calculation time and calculate design conditions x that are the best solution obtained within the corresponding time. The search unit 13 may save all of the solutions obtained within the corresponding time and output all of the solutions at the end.

According to this design support apparatus 1 of the first embodiment, the time required for design can be reduced while also taking into account the production conditions of the metal material. In greater detail, the design support apparatus 1 calculates the characteristic values of steel material using the trained prediction model constructed by the prediction model construction unit 12, for example, based on past performance data associating design conditions with the characteristic values of steel material. In this way, the design support apparatus 1 can rapidly calculate the characteristic values of steel material based on numerous design conditions and can perform a thorough search even within a predetermined time. The design support apparatus 1 can search for design conditions corresponding to excellent characteristic values of the steel material.

With the design support apparatus 1, the optimal design conditions corresponding to the desired conditions satisfy constraint conditions, such as those indicated by Expression 1, thereby allowing the design conditions obtained by back analysis to be used effectively even if there are limits on the amount of additives added to the steel material from the perspective of production costs or limits on the capabilities of production equipment. By setting constraint conditions, the design support apparatus 1 can efficiently search within the range of constraint conditions, rather than searching in the dark.

In the first embodiment, the design support apparatus 1 has been described as integrally including the prediction model construction unit 12 that constructs the prediction model, but the design support apparatus 1 is not limited to this configuration. The design support apparatus 1 need not include the prediction model construction unit 12. In other words, the design support apparatus 1 need not include the acquisition interface 11 and a function relating to constructing a prediction model using the prediction model construction unit 12. In this case, an external apparatus that includes components corresponding to the acquisition interface 11 and the prediction model construction unit 12 can acquire the above-described performance data and generates a prediction model, and the design support apparatus 1 can acquire the prediction model from the external apparatus by any appropriate method.

In the first embodiment, the search unit 13 has been described as searching for optimal design conditions within a range that satisfies the constraint conditions, but this example is not limiting. For example, when there is no limit on the amount of additives added to the steel material or the capabilities of the production equipment, the search unit 13 may solve the optimization problem of Expression 1 without acquiring constraint conditions from the acquisition interface 11 or taking constraint conditions into account.

In Expression 1, the evaluation function is represented as the weighted sum of the maximum or minimum of each characteristic, but the content of Expression 1 is not limited to this example. Expression 1 may be replaced by Expression 2 below, based on a reference value $ref_k$ of each characteristic.

$$\min. \sum_k \alpha_k (ref_k - f_k(x))^2 \qquad \text{(Expression 2)}$$

With Expression 2, the search unit 13 can also search for design conditions that have a higher evaluation as the reference value $ref_k$ of each characteristic is approached.

Second Embodiment

A second embodiment of the present disclosure is now described. The configuration and basic functions of the design support apparatus 1 according to the second embodiment are the same as the aforementioned content of the first embodiment, described with reference to FIGS. 1 through 5. Accordingly, the content corresponding to the explanation in the first embodiment also applies to the second embodiment. Elements that are the same as in the first embodiment are labeled with the same reference signs, and an explanation thereof is omitted. The points that differ from the first embodiment are mainly described below. Unlike the first embodiment, deviation among the predicted values of characteristics due to training data in the evaluation function of Expression 1 is taken into consideration in the second embodiment. In the present disclosure, "deviation among predicted values" includes, for example, deviation among a plurality of predicted values based on a plurality of different training data sets.

For example, when there is sufficient data to guarantee the accuracy of the prediction model in all search areas, an increase in deviation among predicted values relative to measured values with regard to the characteristics of steel material can be suppressed. When the search unit 13 searches in an area of design that has not yet been implemented, however, there is a risk of such an increase in the deviation among predicted values due to the training data. The design support apparatus 1 according to the second embodiment therefore solves the optimization problem by changing Expression 1 to the following problem settings.

$$\max. \sum_k \alpha_k f_k(x) - \sum_k \beta_k V_k(x) \qquad \text{(Expression 3)}$$
$$\text{st.} \quad x \in F$$
$$L_k \leq f_k \leq U_k \quad k = 1..K$$

Here, $V_k(x)$ indicates the "deviation among predicted values" yielded by calculating the instability with which predicted values change due to different training data sets of the prediction model. $\beta_k$ is a weighting factor set in advance. In this way, the evaluation function according to the second embodiment is formed by the weighted sum of two functions.

Figure 6:
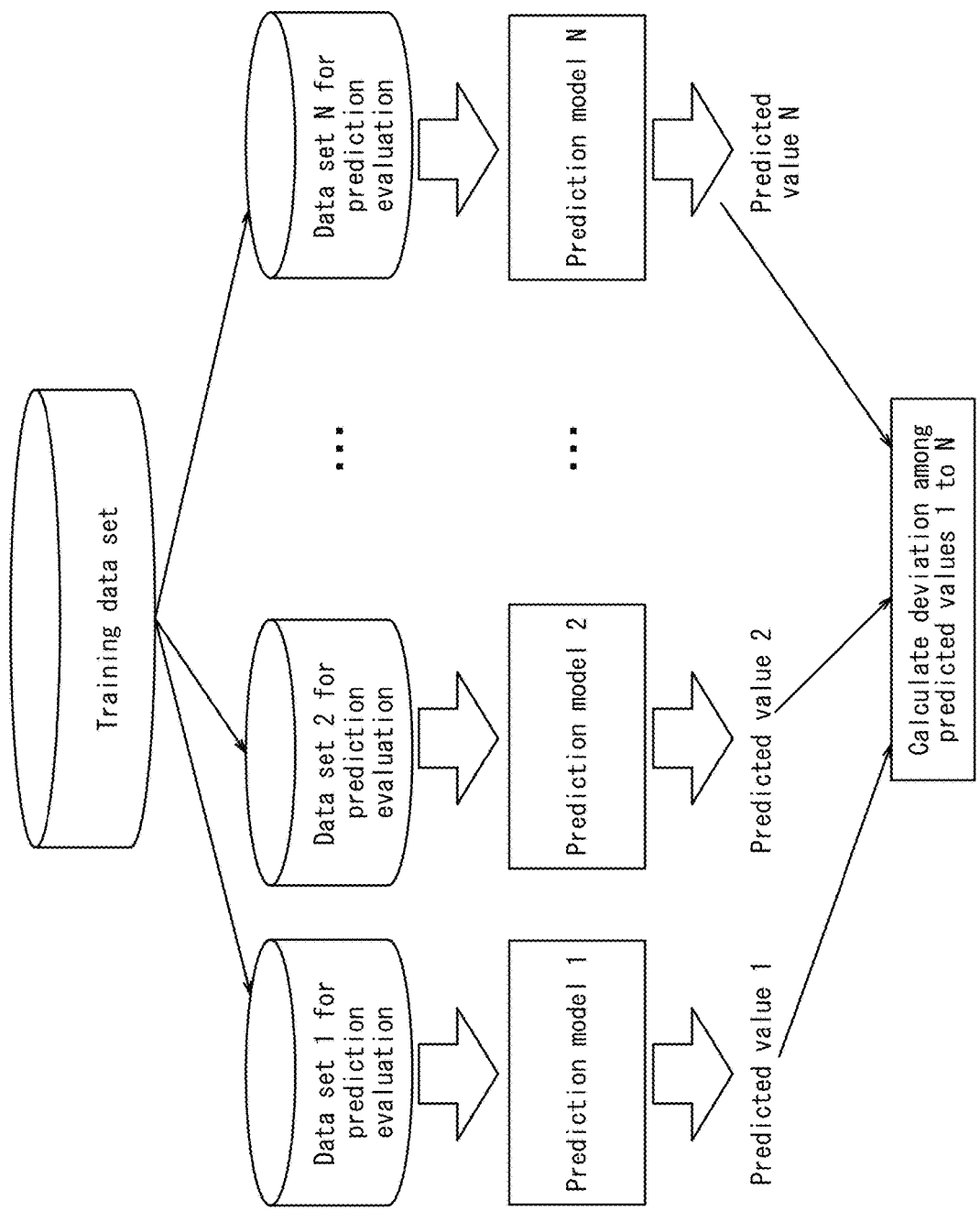
FIG. 6 is a schematic diagram illustrating an example of a method for calculating $V_k(x)$.

FIG. 6 is a schematic diagram illustrating an example of a method for calculating $V_k(x)$. The search unit 13 calculates $V_k(x)$ with any appropriate method, such as the method illustrated in FIG. 6. For example, in the method illustrated in FIG. 6, a plurality of data sets for prediction evaluation are prepared by extracting a plurality of samples at random from a model training data set. Here, the number of extracted samples is a number corresponding to approximately 70% to 90% of the original model training data set. A plurality of prediction models for prediction evaluation are then created using these data sets as training data. The prediction model for prediction evaluation is assumed to be constructed by the prediction model construction unit 12. These prediction models for prediction evaluation are created in advance, before step S203 of FIG. 5, which searches for optimal design conditions. Next, when an evaluation function is calculated for design condition x as in step S203 of FIG. 5, predicted values are calculated using the prediction models for prediction evaluation, and the distribution of the predicted values is taken as $V_k(x)$.

For example, K×N predicted values are obtained by letting the type k of characteristics be a value from 1 to K, and the number i of the prediction model be a value from 1 to N. Predicted values $y_{ik}$, for example, can be represented by a K×N matrix. At this time, $V_k(x)$ is represented by Expression (4) below.

$$V_k(x) = \sum_i (y_{ik} - \overline{y_k})^2 / N \qquad \text{(Expression 4)}$$

The second term in the parentheses on the right hand side of Expression (4) is the average of the predicted values $y_{1k}$ to $y_{Nk}$. In Expression (4), calculation can be performed using the value of the predicted values $y_{ik}$ directly, or calculation can be performed using values that have been normalized by row in a K×N matrix of the predicted values $y_{ik}$, for example.

When the distance $V_k(x)$ of the predicted values is large, a change in data used for training at a certain design condition x leads to a large change in the predicted value as well, and the prediction accuracy worsens. In other words, prediction can be considered unstable. It is thought that these conditions are due to a lack of training data necessary for prediction of the design condition x, which makes prediction dependent on a certain small amount of training data. Accordingly, the characteristic value actually calculated for design condition x and the predicted value of the characteristic calculated by $f_k(x)$ are highly likely to diverge.

On the other hand, when the distribution $V_k(x)$ of the predicted value is small, a similar predicted value is derived even if the data used for training changes. Accordingly, prediction does not depend on a certain small amount of training data, thereby allowing accurate, stable prediction. The predicted value of the characteristic calculated by $f_k(x)$ can therefore be evaluated as being certain.

According to this design support apparatus 1 of the second embodiment, deviation among predicted values due to training data is minimized in step S203 of FIG. 5. By $V_k(x)$ thus being incorporated as an objective function of the aforementioned problem setting to take into account the certainty of the predicted values, not only can good predicted values of characteristic values be searched for, but also searching can be performed while reducing the deviation among predicted values due to training data. This reduces the risk that performance values of characteristics will differ greatly from predicted values of characteristics when the design conditions obtained by searching with the search unit 13 are actually verified. In other words, accurate predicted values can be obtained.

As in the first embodiment, Expression 5 below may be used in place of Expression 3 based on a reference value $ref_k$ of each characteristic.

$$\min. \sum_k \alpha_k (ref_k - f_k(x))^2 + \sum_k \beta_k V_k(x) \qquad \text{(Expression 5)}$$

With Expression 5, the search unit 13 can also search for design conditions that have a higher evaluation as the reference value $ref_k$ of each characteristic is approached and for which the certainty of the predicted values is guaranteed.

In the second embodiment, the deviation among predicted values due to training data has been described as being minimized, but this configuration is not limiting. In step S203 of FIG. 5, design conditions for which deviation among predicted values due to training data is reduced may be searched for. At this time, a predetermined first threshold may be set, for example, and design conditions for which deviation among predicted values due to training data is less than the predetermined first threshold may be searched for. The predetermined first threshold includes a value appropriately set by the design support apparatus 1 or the user, for example.

Third Embodiment

A third embodiment of the present disclosure is now described. The configuration and basic functions of the design support apparatus 1 according to the third embodiment are the same as the aforementioned content of the first embodiment, and the aforementioned content of the second embodiment, described with reference to FIGS. 1 through 6. Accordingly, the content corresponding to the explanation in the first and second embodiments also applies to the third embodiment. Elements that are the same as in the first and second embodiments are labeled with the same reference signs, and an explanation thereof is omitted. The points that differ from the first and second embodiments are mainly described below. Unlike the first and second embodiments, the difference between design conditions subject to searching and design conditions in the past performance data is taken into consideration in the third embodiment.

For example, in the problem setting of the first embodiment, only the predicted values are considered as a plan for the search. In this case, the search unit 13 tends to search in a range near the design conditions that have been implemented before and might not search actively for new design conditions. In the third embodiment, the following function $D(x)$ is incorporated as an objective function of the problem setting so that the search unit 13 more reliably searches actively for new design conditions.

$$\max. \sum_k \alpha_k f_k(x) - \sum_k \beta_k V_k(x) + \gamma D(x) \qquad \text{(Expression 6)}$$

$$\text{st. } x \in F$$

$$L_k \leq f_k \leq U_k \ \ k = 1..K$$

Here, $\gamma$ is a weighting factor set in advance. In this way, the evaluation function is formed by the weighted sum of three functions. $D(x)$ is the magnitude of divergence from the design conditions of the performance data used at the time of prediction model construction and is represented by Expression 7 below, for example.

$$D(x) = \sum_s \sqrt{\sum_i \delta_i (x_i - h_{si})^2} \qquad \text{(Expression 7)}$$

Here, $h_{si}$ represents the $i^{th}$ design condition of the $s^{th}$ piece of performance data. $\delta_i$ is a coefficient for the $i^{th}$ design condition.

Expression 7 represents the sum, for each piece of performance data, of the distance between the design conditions searched for and the design conditions of the performance data used at the time of prediction model creation. With Expression 7, the search unit 13 does not search for design conditions that resemble the performance data, but rather more actively searches in a new area of design conditions that have not yet been implemented. With Expression 6, the difference between the design conditions searched for and the design conditions of past performance data is maximized in step S203 of FIG. 5 within a range in which the deviation among predicted values due to training data is minimized. The search unit 13 may search for design conditions including a new area that differs from past performance data. In this way, the search unit 13 not only searches for good predicted values of characteristics, but can also search more actively in a direction away from previous design conditions while taking into account the certainty of prediction.

When the value of the coefficient $\delta_i$ of a predetermined item among design conditions increases, the search unit 13 can perform a search on the corresponding design condition in a range that is farther away from the performance data than other design conditions. For example, when the user wishes to find a new design condition by making a large change from conventional values to the chemical composition of steel material as the design conditions, rather than changing the production conditions, the coefficient $\delta_i$ related to the production conditions may be decreased, and the coefficient $\delta_i$ related to the chemical composition of steel material may be increased. For example, when the user wishes to find a new design condition by making a large change from conventional values to the production conditions as the design conditions, rather than changing the chemical composition of steel material, the coefficient $\delta_i$ related to the chemical composition of steel material may be decreased, and the coefficient $\delta_i$ related to the production conditions may be increased.

According to this design support apparatus 1 of the third embodiment, the search unit 13 searches more actively for new design conditions in step S203 of FIG. 5. The user can thereby discover design conditions that yield completely new characteristics. This can also increase the degree of design freedom for the user if different design conditions for similar characteristic values can be discovered.

As in the first and second embodiments, Expression 8 below may be used in place of Expression 6 based on a reference value $ref_k$ of each characteristic.

$$\min. \sum_k \alpha_k (ref_k - f_k(x))^2 + \sum_k \beta_k V_k(x) + \gamma/D(x) \quad \text{(Expression 8)}$$

By Expression 8, the search unit 13 can more actively search for an area of design conditions that have not yet been implemented and that have a higher evaluation as the reference value $ref_k$ of each characteristic is approached, while taking into account the certainty of predicted values.

Here, in the third embodiment, an example of adding $D(x)$ to the objective function of the second embodiment has been described, but as a modification, $D(x)$ alone may similarly be added to the objective function of the first embodiment. The evaluation function that replaces Expression 6 in this case is indicated below.

$$\max. \sum_k \alpha_k f_k(x) + \gamma D(x) \quad \text{(Expression 9)}$$
$$\text{st. } x \in F$$
$$L_k \leq f_k \leq U_k \; k = 1, \ldots, K$$

In this case, the difference between the design conditions searched for and the design conditions of past performance data is maximized in step S203 of FIG. 5 when searching for optimal design conditions within a range of constraint conditions. In this way, the search unit 13 not only searches for good predicted values of characteristics, but can also search more actively in a direction away from previous design conditions. The term $V_k(x)$ in Expression 6 is absent in this case, increasing the degree of freedom to search for conditions.

The objective function corresponding to Expression 8 is indicated below.

$$\min. \Sigma_k \alpha_k (ref_k - f_k(x))^2 + \gamma/D(x) \quad \text{(Expression 10)}$$

By Expression 10, the search unit 13 can more actively search for an area of design conditions that have not yet been implemented and that have a higher evaluation as the reference value $ref_k$ of each characteristic is approached, while taking into account the certainty of predicted values.

In the third embodiment, the difference between the design conditions searched for and the design conditions of past performance data has been described as being maximized, but this example is not limiting. In step S203 of FIG. 5, design conditions may be searched for so that the difference between the design conditions searched for and the design conditions of past performance data increases. At this time, a predetermined second threshold may be set, for example, and design conditions may be searched for so that the difference between the design conditions searched for and the design conditions of past performance data exceeds the predetermined second threshold. The predetermined second threshold includes a value appropriately set by the design support apparatus 1 or the user, for example.

Fourth Embodiment

A fourth embodiment of the present disclosure is now described. The configuration and basic functions of the design support apparatus 1 according to the fourth embodiment are the same as the aforementioned content of the first embodiment, and the aforementioned content of the second and third embodiments, described with reference to FIGS. 1 through 6. Accordingly, the content corresponding to the explanation in the first through third embodiments also applies to the fourth embodiment. Elements that are the same as in the first through third embodiments are labeled with the same reference signs, and an explanation thereof is omitted. The points that differ from the first through third embodiments are mainly described below. Unlike the first through third embodiments, image data on the metallic structure of the steel material is used as input to the prediction model illustrated in FIG. 3 in the fourth embodiment.

In the case of steel material, the image data on the metallic structure is required to have a size and resolution enabling the design support apparatus 1 to evaluate the microstructure grain size, microstructure proportion, and the like of the metallic structure, including ferrite, martensite, bainite, and the like, for example. When microstructures such as precipitates are also to be evaluated, the design support apparatus 1 may separately use different image data with a corresponding size and resolution and process a plurality of pieces of image data.

Figure 7:
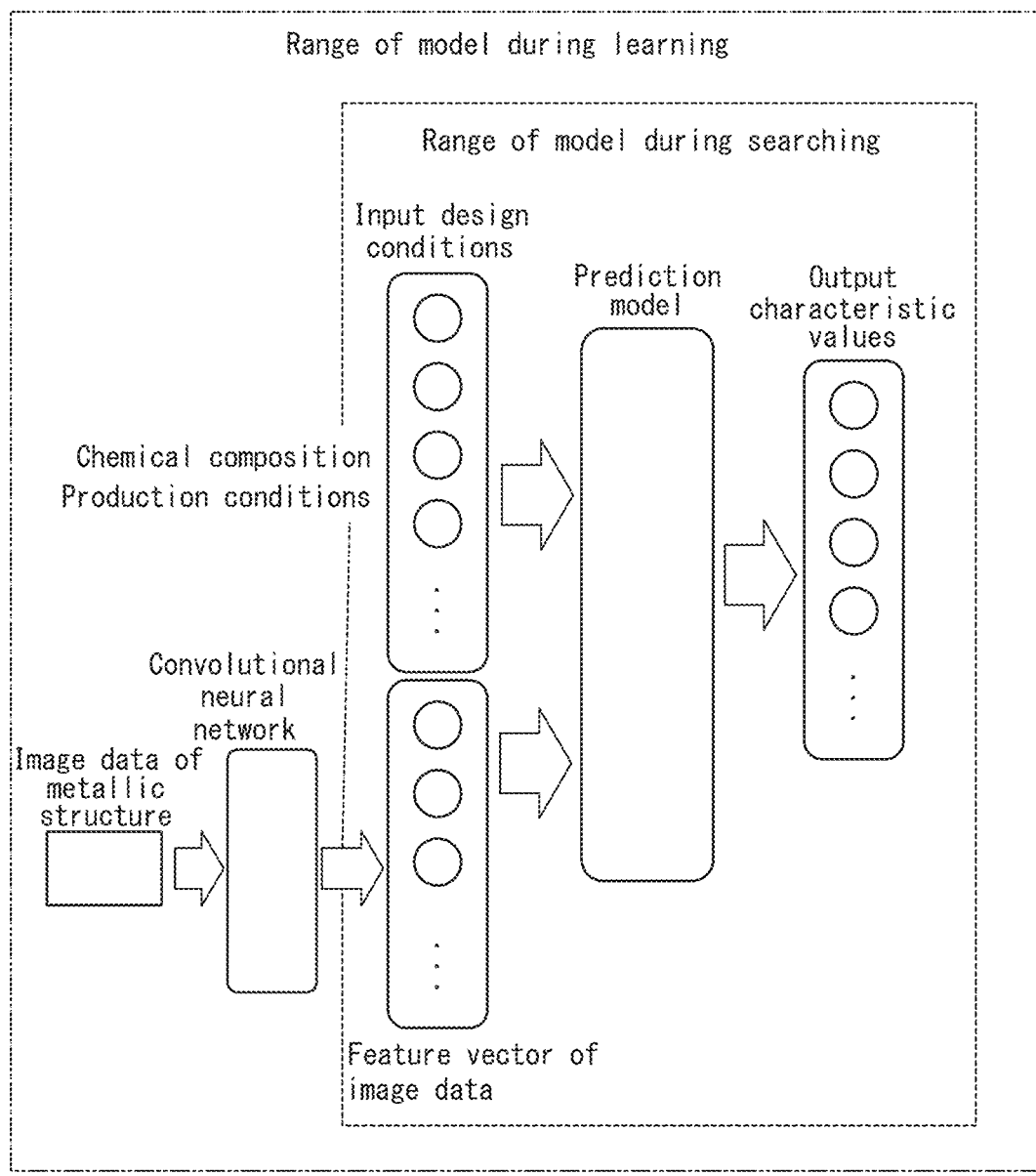
FIG. 7 is a diagram schematically illustrating a prediction model according to a fourth embodiment.

FIG. 7 is a diagram schematically illustrating a prediction model according to the fourth embodiment. In FIG. 7, the prediction model is, for example, a model in which a neural network is used.

The prediction accuracy of the prediction model is important in the search for optimal design conditions. In the first through third embodiments, the acquisition interface 11 acquires the chemical composition and production conditions of steel material, as illustrated in FIG. 3, as the input of the prediction model at the time of learning, but this example is not limiting. In addition to these design conditions, the acquisition interface 11 may also acquire image data on the metallic structure of steel material to use as input for the prediction model at the time of learning in the fourth embodiment, as illustrated in FIG. 7. The prediction model construction unit 12 constructs the prediction model based also on the image data acquired by the acquisition interface 11. The search unit 13 searches for design conditions using this prediction model.

In the case of handling image data as input, the prediction model construction unit 12, for example, quantifies the image data by a predetermined method. If the prediction model construction unit 12 were to extract pixel information of the image as a vector and input the vector, different vector input values would be obtained upon even a slight change in pixel information, even for image data on a metallic structure with identical characteristics. Accordingly, additional parameter learning of the prediction model would occur for each piece of image data for learning, and the learning efficiency would worsen.

To address this issue, the prediction model construction unit 12 uses a convolutional neural network to convert the image data on a metallic structure to a feature vector with fewer features than the number of pixels, for example. The prediction model construction unit 12 treats the converted feature vector as an input value of the prediction model. Image data is thus converted to a lower dimension feature vector. Accordingly, the image data on metallic structures of steel material with similar characteristic values yields the same or similar vectors, and the learning efficiency improves.

Figure 8A:
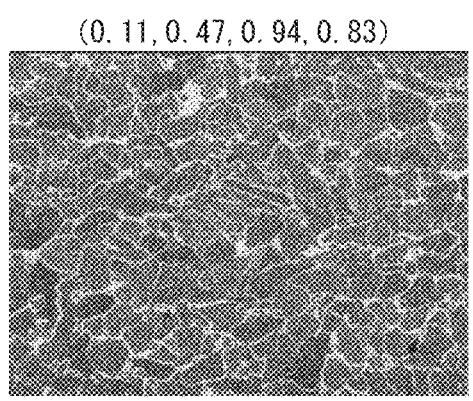
FIG. 8A is a schematic diagram illustrating a first example of the correspondence relationship between image data and a feature vector.
Figure 8B:
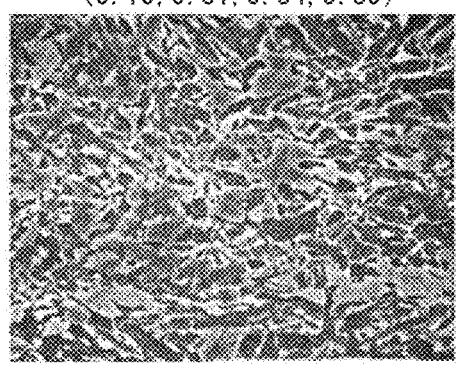
FIG. 8B is a schematic diagram illustrating a second example of the correspondence relationship between image data and a feature vector.
Figure 8C:
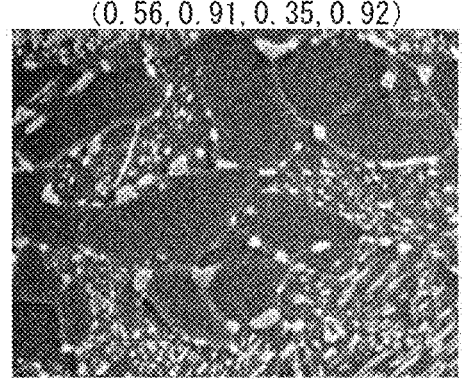
FIG. 8C is a schematic diagram illustrating a third example of the correspondence relationship between image data and a feature vector.
Figure 8D:
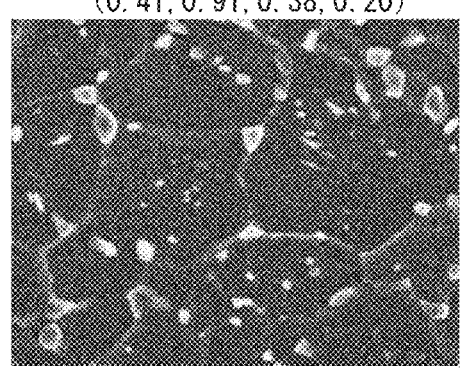
FIG. 8D is a schematic diagram illustrating a fourth example of the correspondence relationship between image data and a feature vector.

FIG. 8A is a schematic diagram illustrating a first example of the correspondence relationship between image data and a feature vector. FIG. 8B is a schematic diagram illustrating a second example of the correspondence relationship between image data and a feature vector. FIG. 8C is a schematic diagram illustrating a third example of the correspondence relationship between image data and a feature vector. FIG. 8D is a schematic diagram illustrating a fourth example of the correspondence relationship between image data and a feature vector. Specific examples when image data is converted to a lower dimension feature vector is mainly described with reference to FIGS. 8A through 8D.

For example, when first image data such as the image data illustrated in FIG. 8A is obtained, the prediction model construction unit 12 uses a convolutional neural network to convert the first image data on a metallic structure to a first feature vector (0.11, 0.47, 0.94, 0.83) with fewer features than the number of pixels.

For example, when second image data such as the image data illustrated in FIG. 8B is obtained, the prediction model construction unit 12 uses a convolutional neural network to convert the second image data on a metallic structure to a second feature vector (0.10, 0.31, 0.54, 0.89) with fewer features than the number of pixels.

For example, when third image data such as the image data illustrated in FIG. 8C is obtained, the prediction model construction unit 12 uses a convolutional neural network to convert the third image data on a metallic structure to a third feature vector (0.56, 0.91, 0.35, 0.92) with fewer features than the number of pixels.

For example, when fourth image data such as the image data illustrated in FIG. 8D is obtained, the prediction model construction unit 12 uses a convolutional neural network to convert the fourth image data on a metallic structure to a fourth feature vector (0.41, 0.91, 0.38, 0.20) with fewer features than the number of pixels.

In FIGS. 8A through 8D, image data on four metallic structures is illustrated, but any number of pieces of image data on metallic structures may be used as input for the prediction model. In FIGS. 8A through 8D, four elements are illustrated for each feature vector, but the feature vectors may have any number of elements.

In addition to the chemical composition and production conditions of steel material, the prediction model construction unit 12 uses image data on the metallic structure as input at the time of learning, uses characteristic values as output, and learns simultaneously including the convolutional neural network portion, as illustrated by the area enclosed by a dashed double-dotted line in FIG. 7. On the other hand, the search unit 13, for example, uses a model that excludes the convolutional neural network portion when searching for design conditions, as illustrated by the area enclosed by a dashed line in FIG. 7. At this time, the aforementioned feature vectors, rather than image data, are included in the design conditions searched for by the search unit 13.

FIG. 9 is a schematic diagram illustrating an example of a method to convert a feature vector into image data. The feature vector obtained by searching with the search unit 13 may be converted to image data by the following method, for example. The search unit 13 calculates the feature vector at the time when image data for training is inputted to the trained model in the same way as FIGS. 8A through 8D, for example. The search unit 13 stores data associating image data and feature vectors in any appropriate storage apparatus. While referring to the storage apparatus, the search unit 13 selects a feature vector, from among the stored feature vectors, that approximates the feature vector included in the design conditions obtained by the search.

For example, the search unit 13 obtains the vector (0.40, 0.90, 0.40, 0.20) as the feature vector included in the design conditions obtained by the search. At this time, while referring to the storage apparatus, the search unit selects the fourth feature vector (0.41, 0.91, 0.38, 0.20), which approximates the feature vector (0.40, 0.90, 0.40, 0.20), from among the stored feature vectors. While referring to the storage apparatus, the search unit 13 outputs the fourth image data on the metallic structure corresponding to the selected fourth feature vector to the presentation interface 14 as design conditions.

According to this design support apparatus 1 of the fourth embodiment, the design conditions searched for in step S203 of FIG. 5 include a feature vector based on image data on the metallic structure of steel material. By using image data on the metallic structure in this way, the design support apparatus 1 can acquire design conditions that, unlike the chemical composition and production conditions of the steel material, are specific to the image data on the metallic structure. The prediction accuracy of the prediction model therefore increases.

At this time, the user does not need to provide the design support apparatus 1 with input of training data indicating which type of parameters related to the metallic structure are obtained for such image data. The design support apparatus 1 can express the difference between pieces of image data on the metallic structure as a difference between feature vectors. Hence, even when not specifically identifying which parameter related to the metallic structure caused the difference, the design support apparatus 1 can reflect such a difference in the characteristic values of the output.

EXAMPLES

Examples of the design of a steel material for a cold-rolled steel sheet for automobiles are illustrated below, based mainly on the third embodiment. In the present Examples, the tensile strength was selected as the characteristic of the steel material, and design conditions including the maximum tensile strength as the desired characteristic value were searched for.

Table 4 lists examples of the steel material chemical composition (unit: mass %) that affects characteristics, Table 5 lists examples of production conditions that affect characteristics, and Table 6 lists examples of types of characteristics and characteristic values. A prediction model that takes design conditions as input and outputs characteristics was constructed by acquiring the performance data items of Tables 4, 5, 6 and performing machine learning using the performance data.

TABLE 4

(units: mass %)

| Steel sample No. | C | Si | Mn | P | S | Al | N | Cr | V | Sb | Mo | Cu | Ni | Ti | Nb | B | Ca |
|---|---|---|---|---|---|---|---|---|---|---|---|---|---|---|---|---|---|
| A | 0.124 | 0.66 | 2.55 | 0.008 | 0.0010 | 0.037 | 0.0034 | 0 | 0 | 0.011 | 0 | 0 | 0 | 0.015 | 0.038 | 0.0016 | 0.0002 |
| B | 0.105 | 0.53 | 2.79 | 0.010 | 0.0008 | 0.035 | 0.0040 | 0 | 0 | 0.010 | 0 | 0 | 0 | 0.014 | 0.042 | 0.0015 | 0.0001 |
| C | 0.131 | 0.56 | 2.57 | 0.009 | 0.0011 | 0.042 | 0.0036 | 0.05 | 0 | 0.009 | 0 | 0 | 0 | 0.017 | 0.034 | 0.0017 | 0.0001 |

TABLE 5

| | | Hot rolling conditions | | | | Continuous annealing conditions | | | | | | | | |
|---|---|---|---|---|---|---|---|---|---|---|---|---|---|---|
| Steel plate No. | Steel sample No. | Heating temp. (° C.) | Finish rolling temp. (° C.) | Coiling temp. (° C.) | Sheet thickness (mm) | Average heating rate (° C./s) until temp. region of 570° C. or higher | Heating temp. (° C.) | Soaking temp. (° C.) | Holding time (s) at temp. region of Ac3 or higher | Average cooling rate (° C./s) until temp. region of 620° C. to 740° C. | Cooling stop temp. (° C.) | Holding time (s) at temp. region of 620° C. to 740° C. | Average cooling rate (° C./s) until temp. region of 400° C. or lower | Cooling stop temp. (° C.) | Holding time (s) at temp. region of 150° C. or higher and 400° C. or lower |
| 1 | A | 1240 | 880 | 560 | 1.4 | 4 | 620 | 860 | 140 | 1.8 | 660 | 18 | 37 | 280 | 430 |
| 2 | B | 1240 | 880 | 560 | 1.4 | 4 | 630 | 860 | 110 | 3.4 | 680 | 37 | 18 | 310 | 510 |
| 3 | C | 1240 | 880 | 560 | 1.4 | 4 | 620 | 850 | 120 | 1.5 | 680 | 22 | 22 | 260 | 470 |

TABLE 6

| Steel sheet No. | Steel sample No. | Tensile strength (MPa) |
|---|---|---|
| 1 | A | 1283 |
| 2 | B | 1205 |
| 3 | C | 1247 |

Figure 10:
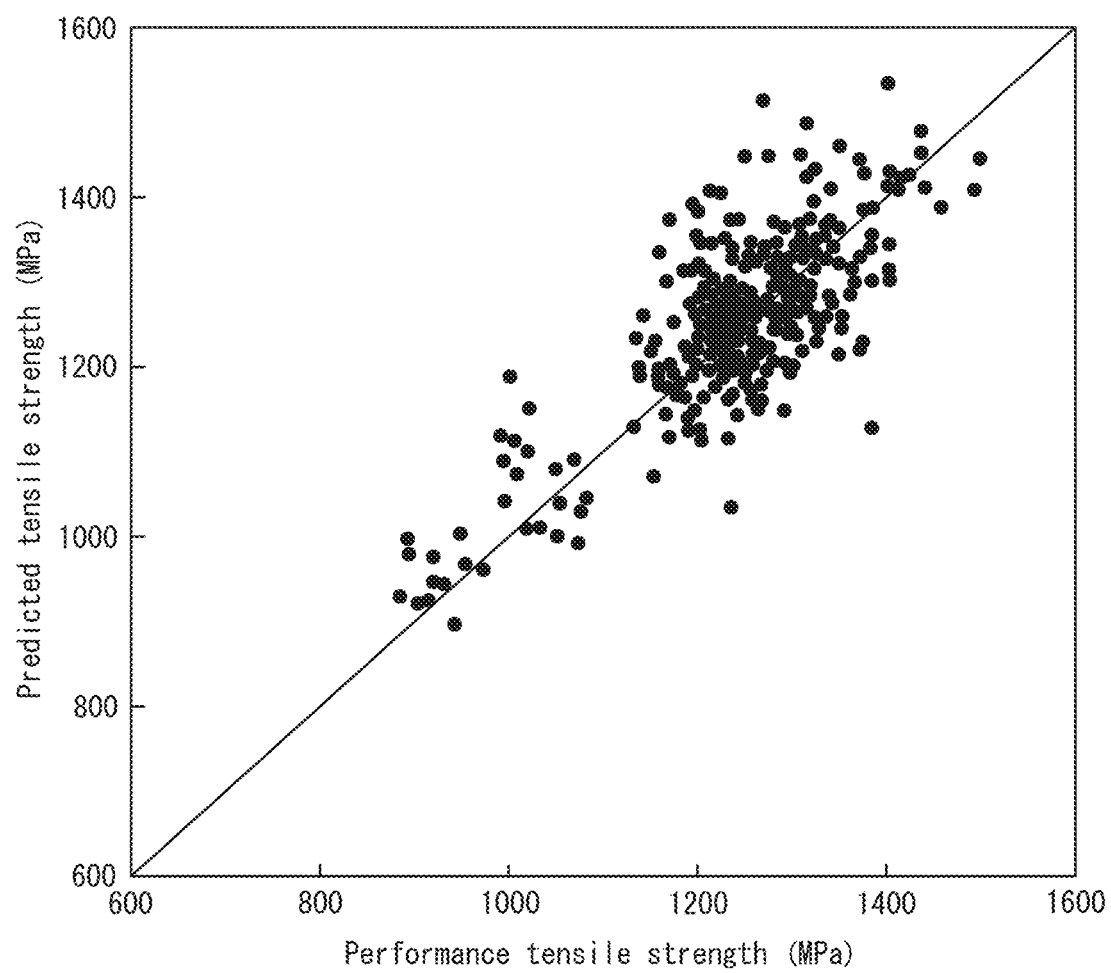
FIG. 10 is a distribution diagram for performance values and predicted values of tensile strength.

In the present Examples, 500 pieces of training data were used, a machine learning method known as a neural network was used, and a prediction model to predict tensile strength as a characteristic was created. FIG. 10 is a distribution diagram for performance values and predicted values of tensile strength. The horizontal axis in the distribution diagram represents the performance value of tensile strength, and the vertical axis represents the predicted value of tensile strength. The number of hidden layers in the neural network was one, and the number of nodes was 15. The value of each explanatory variable was standardized. The prediction accuracy was 71.94 by root mean square error (RMSE).

Table 7 lists the constraint conditions on design conditions used when searching for design conditions.

TABLE 7

| Production process | Design condition | Lower limit value | Upper limit value |
|---|---|---|---|
| Converter/ secondary refining | C (mass %) | 0.041 | 0.212 |
| | Si (mass %) | 0.048 | 0.79 |
| | Mn (mass %) | 1.94 | 3.34 |
| | P (mass %) | 0.006 | 0.043 |
| | S (mass %) | 0.0006 | 0.0043 |
| | Al (mass %) | 0.0248 | 0.067 |
| | N (mass %) | 0.0022 | 0.00564 |
| | Cr (mass %) | 0 | 0.3 |
| | V (mass %) | 0 | 0.11 |
| | Sb (mass %) | 0.0008 | 0.018 |
| | Mo (mass %) | 0 | 0.21 |
| | Cu (mass %) | 0 | 0.096 |
| | Ni (mass %) | 0 | 0.084 |
| | Ti (mass %) | 0.008 | 0.032 |
| | Nb (mass %) | 0.015 | 0.056 |
| | B (mass %) | 0.0002 | 0.0031 |
| | Ca (mass %) | 0.00008 | 0.0016 |
| Heating process/ hot rolling Annealing process | Heating temperature (° C.) | 960 | 1500 |
| | Finish rolling temperature (° C.) | 512 | 1068 |
| | Coiling temperature (° C.) | 408 | 852 |
| | Sheet thickness (mm) | 1.12 | 2.4 |
| | Average heating rate (° C./s) until temp. region of. 570° C or higher | 1.6 | 20 |
| | Heating temp. (° C.) | 400 | 780 |
| | Soaking temp. (° C.) | 568 | 1056 |
| | Holding time (s) at temp. region of Ac3 orhigher | 28 | 216 |
| | Average cooling rate (° C./s) until temp. region of 620° C. to 740° C. | 0.64 | 27.24 |
| | Cooling stop temp. (° C.) | 456 | 960 |
| | Holding time (s) at temp. region of 620° C. to 740° C. | 3.2 | 156 |
| | Average cooling rate (° C./s) until temp. region of 400° C. or lower | 2.4 | 96 |
| | Cooling stop temp. (° C.) | 168 | 684 |
| | Holding time (s) at temp. region of 150° C. or higher and 400° C. or lower | 128 | 936 |

As can be seen from Table 7, the constraint conditions include the range of the chemical composition of the steel material and the range of production conditions. Additionally, the constraint conditions include conditions guaranteeing no contradictions among changes, occurring between different processes during production, in physical quantities of a steel sheet. For example, the constraint conditions may include the condition of heating temperature>finish rolling temperature>coiling temperature.

Table 8 lists the constraint conditions on characteristic values used when searching for design conditions.

TABLE 8

| Characteristic | Lower limit value | Upper limit value |
|---|---|---|
| Tensile strength (MPa) | 1300 | 1600 |

A trained prediction model and constraint conditions (F, $L_k$, $U_k$) were thus obtained. The design support apparatus 1 then searched for optimal design conditions as an optimization problem, such as the optimization problem in Expressions 6 and 7 of the third embodiment, and obtained design conditions corresponding to good characteristic values. The design support apparatus 1 used particle swarm optimization, a type of swarm intelligence, as a search algorithm. The number of particles was 1000, and the number of solution updates was 500. The weighting factors of the optimization problem were $\alpha=1$, $\beta=6.0$, and $\gamma=0.5$. The number of models used to calculate V(x) was 50, and learning was performed by selecting 80% of the training data at random. Furthermore, with regard to $\delta_i$ in D(x) of Expression 7, the $\delta_i$ for the design condition regarding the chemical composition of the steel material was 1, and the $\delta_i$ for the production condition was 0. Here, the calculation of D(x) uses standardized values.

Table 9 illustrates the design conditions searched for by the design support apparatus 1. The tensile strength under these design conditions was 1545 MPa, and the maximum tensile strength in the performance data was 1498 MPa. Hence, new design conditions included in a new search area with a higher tensile strength were discovered.

TABLE 9

| Production process | Design condition | Predicted value |
|---|---|---|
| Converter/ secondary refining | C (mass %) | 0.167 |
| | Si (mass %) | 0.51 |
| | Mn (mass %) | 2.66 |
| | P (mass %) | 0.018 |
| | S (mass %) | 0.0028 |
| | Al (mass %) | 0.053 |
| | N (mass %) | 0.0037 |
| | Cr (mass %) | 0.10 |
| | V (mass %) | 0.073 |
| | Sb (mass %) | 0.010 |
| | Mo (mass %) | 0.060 |
| | Cu (mass %) | 0.036 |
| | Ni (mass %) | 0.033 |
| | Ti (mass %) | 0.016 |
| | Nb (mass %) | 0.046 |
| | B (mass %) | 0.002 |
| | Ca (mass %) | 0.0010 |
| Heating process/ hot rolling | Heating temperature (° C.) | 1218 |
| | Finish rolling temperature (° C.) | 761 |
| | Coiling temperature (° C.) | 542 |
| Annealing process | Sheet thickness (mm) | 1.4 |
| | Average heating rate (° C./s) until temp. region of 570° C. or higher | 13 |
| | Heating temp. (° C.) | 616 |
| | Soaking temp. (° C.) | 847 |
| | Holding time (s) at temp. region of Ac3 or higher | 115 |
| | Average cooling rate (° C./s) until temp. region of 620° C. to 740° C. | 12.7 |
| | Cooling stop temp. (° C.) | 690 |
| | Holding time (s) at temp. region of 620° C. to 740° C. | 69 |

TABLE 9-continued

| Production process | Design condition | Predicted value |
|---|---|---|
| | Average cooling rate (° C./s) until temp. region of 400° C. or lower | 15 |
| | Cooling stop temp. (° C.) | 287 |
| | Holding time (s) at temp. region of 150° C. or higher and 400° C. or lower | 539 |

Table 10 is a comparison between the results when the optimization problem was similarly solved with the first and second embodiments and the above-described results with the third embodiment. The setting $\alpha=1$ was used in the first embodiment. The settings $\alpha=1$ and $\beta=6.0$ were used in the second embodiment. The constraint conditions and the parameters of particle swarm optimization were the same as in the above-described case for the third embodiment.

TABLE 10

| | First embodiment | Second embodiment | Third embodiment |
|---|---|---|---|
| Tensile strength (f(x)) (MPa) | 1599 | 1533 | 1545 |
| Variation in predicted values (V(x)) | 989 | 201 | 221 |
| Distance from performance data (D(x)) | 741 | 628 | 661 |

In the first embodiment, searching for design characteristics corresponding to a high tensile strength tended to increase the deviation among the predicted values of the characteristics, increasing the risk of a difference between the performance value and the predicted value of the tensile strength. On the other hand, as compared to the first embodiment that does not take deviation among predicted values into consideration, design conditions with little deviation among predicted values are searched for in the second embodiment. Furthermore, it is clear that in the third embodiment, the deviation among predicted values is suppressed, and design conditions can be searched for in a search area more distant from the performance data than in the second embodiment.

Although the matter of the present disclosure has been explained with reference to the accompanying drawings and examples, it is to be noted that various changes and modifications will be apparent to those of ordinary skill in the art based on the present disclosure. Therefore, such changes and modifications are to be understood as included within the scope of the present disclosure. For example, the functions and the like included in the various means and steps may be reordered in any logically consistent way. Furthermore, means and steps may be combined into one or divided.

For example, the present disclosure may also be embodied as a program containing a description of the processing for achieving the functions of the above-described design support apparatus 1 or a storage medium with the program recorded thereon. These embodiments are also to be understood as included in the scope of the present disclosure.

REFERENCE SIGNS LIST

1 Design support apparatus
11 Acquisition interface
12 Prediction model construction unit
13 Search unit
14 Presentation interface

The invention claimed is:

1. A design support method carried out by a design support apparatus comprising a processor, an acquisition interface, and a display for supporting design, of a metal material that has desired characteristics, the design support method comprising:
acquiring, by the processor via the acquisition interface, constraint conditions as input information, the constraint conditions including a range of a chemical composition of the metal material and a range of production conditions of the metal material;
searching, by the processor, for design conditions that satisfy the constraint conditions and yield the desired characteristics using a prediction model for predicting a characteristic value of the metal material from the design conditions, the prediction model being constructed based on past performance data associating the design conditions, which include the chemical composition and production conditions of the metal material, with the characteristic value; and
displaying, by the processor via the display, at least the chemical composition and the production conditions among the design conditions that are searched for by the processor and correspond to the desired characteristics, wherein
the design conditions are searched for so that deviation among a plurality of predicted values based on a plurality of different training data sets is reduced, the deviation among the plurality of predicted values indicating a degree of difference of the predicted value from an average value of the plurality of predicted values, and
the metal material is produced based on at least the chemical composition and the production conditions.

2. The design support method of claim 1, wherein
the design conditions that are searched for and correspond to the desired characteristics satisfy the constraint conditions.

3. The design support method of claim 1, wherein the design conditions are also searched for in a new area differing from the past performance data so that a difference between the design conditions that are searched for and the design conditions in the past performance data increases.

4. The design support method of claim 1, wherein
the design conditions include a feature vector based on image data of a metallic structure of the metal material, and
the design conditions that are searched for include the feature vector.

5. A prediction model generation method for generating the prediction model used in the design support method of claim 1, the prediction model generation method comprising:
acquiring the past performance data associating the design conditions with the characteristic value; and
constructing the prediction model, for predicting the characteristic value from the design conditions, based on the acquired past performance data.

6. A design support apparatus for supporting design of a metal material that has desired characteristics, the design support apparatus comprising:
an acquisition interface configured to acquire constraint conditions as input information, the constraint conditions including a range of a chemical composition of the metal material and a range of production conditions of the metal material;
a processor configured to search for design conditions that satisfy the constraint conditions and yield the desired characteristics using a prediction model for predicting a characteristic value of the metal material from the design conditions, the prediction model being constructed based on past performance data associating the design conditions, which include the chemical composition and production conditions of the metal material, with the characteristic value; and
a display configured to display at least the chemical composition and the production conditions among the design conditions, searched for by the processor, that correspond to the desired characteristics, wherein
the processor searches for the design conditions so that deviation among a plurality of predicted values based on a plurality of different training data sets is reduced, the deviation among the plurality of predicted values indicating a degree of difference of the predicted value from an average value of the plurality of predicted values, and
the metal material is produced based on at least the chemical composition and the production conditions.

7. The design support method of claim 2, wherein the design conditions are also searched for in a new area differing from the past performance data so that a difference between the design conditions that are searched for and the design conditions in the past performance data increases.

8. The design support method of claim 2, wherein
the design conditions include a feature vector based on image data of a metallic structure of the metal material, and
the design conditions that are searched for include the feature vector.

9. The design support method of claim 3, wherein
the design conditions include a feature vector based on image data of a metallic structure of the metal material, and
the design conditions that are searched for include the feature vector.

10. A prediction model generation method for generating the prediction model used in the design support method of claim 4, the prediction model generation method comprising:
acquiring the past performance data associating the design conditions with the characteristic value; and
constructing the prediction model, for predicting the characteristic value from the design conditions, based on the acquired past performance data.

* * * * *